United States Patent
Regad

(10) Patent No.: US 12,221,490 B2
(45) Date of Patent: Feb. 11, 2025

(54) ANTIBODIES AGAINST HEPCR

(71) Applicant: NOTTINGHAM TRENT UNIVERSITY, Nottingham (GB)

(72) Inventor: Tarik Regad, Nottingham (GB)

(73) Assignee: NOTTINGHAM TRENT UNIVERSITY, Nottingham (GB)

( * ) Notice: Subject to any disclaimer, the term of this patent is extended or adjusted under 35 U.S.C. 154(b) by 819 days.

(21) Appl. No.: 17/428,816

(22) PCT Filed: Feb. 3, 2020

(86) PCT No.: PCT/GB2020/050244
§ 371 (c)(1),
(2) Date: Aug. 5, 2021

(87) PCT Pub. No.: WO2020/161478
PCT Pub. Date: Aug. 13, 2020

(65) Prior Publication Data
US 2022/0127374 A1    Apr. 28, 2022

(30) Foreign Application Priority Data

Feb. 6, 2019 (GB) .................. 1901640

(51) Int. Cl.
*C07K 16/30* (2006.01)
*A61P 35/00* (2006.01)
*C07K 16/28* (2006.01)

(52) U.S. Cl.
CPC .......... *C07K 16/3069* (2013.01); *A61P 35/00* (2018.01); *C07K 16/2869* (2013.01)

(58) Field of Classification Search
CPC ............ C07K 16/3069; C07K 16/2869; C07K 2317/732; C07K 16/2896; C07K 16/30; A61P 35/00; A61K 39/39558
See application file for complete search history.

(56) References Cited

FOREIGN PATENT DOCUMENTS

| CN | 106267187 A | 1/2017 |
| CN | 107502658 A | 12/2017 |
| JP | 2005035943 A | 2/2005 |
| JP | 2005206508 A | 8/2005 |
| WO | 2016026444 A1 | 2/2016 |

OTHER PUBLICATIONS

Mohan Rao LV, Esmon CT, Pendurthi UR. Endothelial cell protein C receptor: a multiliganded and multifunctional receptor. Blood. Sep. 4, 2014;124(10):1553-62. (Year: 2014).*
Florence Schaffner et al: "Endothelial Protein C Receptor Function in Murine and Human Breast Cancer Development", PLOS ONE, vol. 8, No. 4, Apr. 1, 2013 (Apr. 1, 2013), p. e61071, XP055678723.
Menschikowski et al., Cancer Cell International, vol. 11, 2011, "Expression and shedding of endothelial protein C receptor in prostate cancer cells", article No. 4. See Results and Figure 2.
International Search Report and Written Opinion for corresponding PCT application No. PCT/GB2020/050244, mailed Jun. 25, 2020.
UK Search Report for corresponding GB patent application No. GB1901640.1, dated Jun. 28, 2019.

* cited by examiner

*Primary Examiner* — Brad Duffy
*Assistant Examiner* — Amber K Faust
(74) *Attorney, Agent, or Firm* — Notaro, Michalos & Zaccaria P.C.

(57) ABSTRACT

An antibody or antigen-binding fragment that binds human endothelial protein C receptor (hEPCR) and neutralizes, reduces or interferes with at least one activity of hEPCR, in which (a) the antibody or antigen-binding fragment has a heavy chain variable region (HCVR) with at least 80% identity to a sequence selected from SEQ ID NO: 1, 3, 5 and 7, and/or a light chain variable region (LCVR) with at least 80% identity to a sequence selected from SEQ ID NO: 2, 4, 6 and 8, and/or (b) the antibody or antigen-binding fragment has a heavy chain variable region (HCVR) selected from SEQ ID NO: 1, 3, 5 and 7 with 10 or fewer conservative amino acid substitutions and/or a light chain variable region (LCVR) selected from SEQ ID NO: 2, 4, 6 and 8 with 10 or fewer conservative amino acid substitutions, is disclosed.

12 Claims, 4 Drawing Sheets

Specification includes a Sequence Listing.

| Antibody | EC$_{50}$ (µg/ml) | Maximum Fold Induction |
|---|---|---|
| H61.3 | 2.095 | 91.77 |
| H589.9 | 5.967 | 21.09 |
| H599.5 | 2.027 | 42.58 |
| H754.6 | 4.331 | 56.8 |

| Antibody | EC$_{50}$ (μg/ml) | Maximum Fold Induction |
|---|---|---|
| H61.3 | 1.99 | 71.63 |
| H589.9 | 14.22 | 17.83 |
| H599.5 | 2.964 | 55.99 |
| H754.6 | 3.657 | 31.48 |

Fig.7

SEQUENCE LISTING

<160> NUMBER OF SEQ ID NOS: 33

<210> SEQ ID NO 1
<211> LENGTH: 120
<212> TYPE: PRT
<213> ORGANISM: Artificial Sequence
<220> FEATURE:
<223> OTHER INFORMATION: Amino acid sequence of clone H61.3 heavy chain variable region

<400> SEQUENCE: 1

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gln Leu Ile Ala Ser Ser Tyr Ala Phe Asp Ile Trp Gly Gln
            100                 105                 110

Gly Thr Met Val Thr Val Ser Ser
```

-continued

```
                115                 120

<210> SEQ ID NO 2
<211> LENGTH: 107
<212> TYPE: PRT
<213> ORGANISM: Artificial Sequence
<220> FEATURE:
<223> OTHER INFORMATION: Amino acid sequence of clone H61.3 variable
      chain light region

<400> SEQUENCE: 2

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Thr Thr Arg
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Thr
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Phe
                85                  90                  95

Thr Phe Gly Pro Gly Thr Lys Val Asp Ile Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence of clone H589.9 variable
      chain heavy region

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ser Ser Gly Ser Gly Gly Ser Ala Phe Tyr Ala Asp Phe Val
    50                  55                  60

Lys Gly Arg Phe Thr Ile Ser Arg Asp Ile Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Glu Gly Thr Ile Ser Met Ala Phe Asp Ile Trp Gly Gln Gly
            100                 105                 110

Thr Thr Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Amino acid sequence of clone H589.9 variable
      chain light region

<400> SEQUENCE: 4
```

```
Ala Ile Gln Met Thr Gln Ser Pro Ser Ser Leu Ser Ala Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Leu Leu Ile
            35                  40                  45

Cys Ala Ala Ser Ser Leu Gln Ser Gly Val Pro Ser Arg Phe Ser Gly
50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
                100                 105
```

<210> SEQ ID NO 5
<211> LENGTH: 121
<212> TYPE: PRT
<213> ORGANISM: Artificial Sequence
<220> FEATURE:
<223> OTHER INFORMATION: Amino acid sequence of clone H599.5 variable
      chain heavy region

<400> SEQUENCE: 5

```
Gln Val Gln Leu Gln Glu Ser Gly Pro Gly Leu Val Gln Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gln Val Asn Gly Trp Tyr Arg Thr Gly Phe Asp Tyr Trp Gly
                100                 105                 110

Gln Gly Thr Leu Val Thr Val Ser Ser
        115                 120
```

<210> SEQ ID NO 6
<211> LENGTH: 108
<212> TYPE: PRT
<213> ORGANISM: Artificial Sequence
<220> FEATURE:
<223> OTHER INFORMATION: Amino acid sequence of clone H599.5 variable
      chain light region

<400> SEQUENCE: 6

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
50                  55                  60
```

Gly Ser Gly Ser Gly Thr Asp Phe Thr Leu Thr Ile Ser Ser Leu Gln
65                  70                  75                  80

Pro Glu Asp Phe Ala Ala Tyr Tyr Cys Gln Gln Asp Tyr Asn Leu Pro
                85                  90                  95

Tyr Thr Phe Gly Arg Gly Ser Lys Leu Glu Ile Lys
            100                 105

<210> SEQ ID NO 7
<211> LENGTH: 120
<212> TYPE: PRT
<213> ORGANISM: Artificial Sequence
<220> FEATURE:
<223> OTHER INFORMATION: Amino acid sequence of clone H754.6 variable
      chain heavy region

<400> SEQUENCE: 7

Gln Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Asn Ser Gly Tyr Thr Ile Tyr Tyr Ala Glu Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Val Ser Phe Tyr Tyr Gly Leu Asp Val Trp Gly Gln
            100                 105                 110

Gly Thr Thr Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: Amino acid sequence of clone H754.6 variable
      chain light region

<400> SEQUENCE: 8

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Gln Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 9

```
<211> LENGTH: 5
<212> TYPE: PRT
<213> ORGANISM: Artificial Sequence
<220> FEATURE:
<223> OTHER INFORMATION: Amino acid sequence of clone H61.3 variable
      chain heavy region CDR1

<400> SEQUENCE: 9

Gly Tyr Tyr Trp Ser
1               5

<210> SEQ ID NO 10
<211> LENGTH: 16
<212> TYPE: PRT
<213> ORGANISM: Artificial Sequence
<220> FEATURE:
<223> OTHER INFORMATION: Amino acid sequence of clone H61.3 variable
      chain heavy region CDR2

<400> SEQUENCE: 10

Glu Ile Asn His Ser Gly Ser Thr Asn Tyr Asn Pro Ser Leu Lys Ser
1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: Amino acid sequence of clone H61.3 variable
      chain heavy region CDR3

<400> SEQUENCE: 11

Arg Gln Leu Ile Ala Ser Ser Tyr Ala Phe Asp Ile
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Amino acid sequence of clone H61.3 variable
      chain light region CDR1

<400> SEQUENCE: 12

Arg Ala Ser Gln Ser Val Thr Thr Arg Tyr Leu Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Amino acid sequence of clone H61.3 variable
      chain light region CDR2

<400> SEQUENCE: 13

Gly Ala Ser Thr Arg Ala Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Amino acid sequence of clone H61.3 variable
      chain light region CDR3

<400> SEQUENCE: 14
```

```
Gln Gln Asp Tyr Asn Leu Phe Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Amino acid sequence of clone H589.9 variable
      region heavy chain CDR1

<400> SEQUENCE: 15

Ser Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Amino acid sequence of clone H589.9 variable
      region heavy chain CDR2

<400> SEQUENCE: 16

Gly Ser Ser Gly Ser Gly Gly Ser Ala Phe Tyr Ala Asp Phe Val Lys
1               5                   10                  15
Gly

<210> SEQ ID NO 17
<211> LENGTH: 10
<212> TYPE: PRT
<213> ORGANISM: Artificial Sequence
<220> FEATURE:
<223> OTHER INFORMATION: Amino acid sequence of clone H589.9 variable
      region heavy chain CDR3

<400> SEQUENCE: 17

Glu Gly Thr Ile Ser Met Ala Phe Asp Ile
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Amino acid sequence of clone H589.9 variable
      region light chain CDR1

<400> SEQUENCE: 18

Arg Ala Ser Gln Gly Ile Arg Asn Asp Leu Gly
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Amino acid sequence of clone H589.9 variable
      region light chain CDR2

<400> SEQUENCE: 19

Ala Ala Ser Ser Leu Gln Ser
1               5

<210> SEQ ID NO 20
<211> LENGTH: 9
<212> TYPE: PRT
```

```
<213> ORGANISM: Artificial Sequence
<220> FEATURE:
<223> OTHER INFORMATION: Amino acid sequence of clone H589.9 variable
      region light chain CDR3

<400> SEQUENCE: 20

Leu Gln Asp Tyr Asn Tyr Pro Arg Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Amino acid sequence of clone H599.5 variable
      region heavy chain CDR1

<400> SEQUENCE: 21

Ser Tyr Tyr Trp Ser
1               5

<210> SEQ ID NO 22
<211> LENGTH: 16
<212> TYPE: PRT
<213> ORGANISM: Artificial Sequence
<220> FEATURE:
<223> OTHER INFORMATION: Amino acid sequence of clone H599.5 variable
      region heavy chain CDR2

<400> SEQUENCE: 22

Tyr Ile Tyr Tyr Ser Gly Ser Thr Asn Tyr Asn Pro Ser Leu Lys Ser
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: Amino acid sequence of clone H599.5 variable
      region heavy chain CDR3

<400> SEQUENCE: 23

Asp Gln Val Asn Gly Trp Tyr Arg Thr Gly Phe Asp Tyr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Amino acid sequence of clone H599.5 variable
      region light chain CDR1

<400> SEQUENCE: 24

Arg Ala Ser Gln Ser Val Ser Ser Gly Tyr Leu Ser
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Amino acid sequence of clone H599.5variable
      region light chain CDR2

<400> SEQUENCE: 25

Gly Ala Ser Thr Arg Ala Thr
1               5
```

```
<210> SEQ ID NO 26
<211> LENGTH: 9
<212> TYPE: PRT
<213> ORGANISM: Artificial Sequence
<220> FEATURE:
<223> OTHER INFORMATION: Amino acid sequence of clone H599.5 variable
      region light chain CDR3

<400> SEQUENCE: 26

Gln Gln Asp Tyr Asn Leu Pro Tyr Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Amino acid sequence of clone H754.6 variable
      region heavy chain CDR1

<400> SEQUENCE: 27

Asp Tyr Tyr Met Thr
1               5

<210> SEQ ID NO 28
<211> LENGTH: 17
<212> TYPE: PRT
<213> ORGANISM: Artificial Sequence
<220> FEATURE:
<223> OTHER INFORMATION: Amino acid sequence of clone H754.6 variable
      region heavy chain CDR2

<400> SEQUENCE: 28

Tyr Ile Ser Asn Ser Gly Tyr Thr Ile Tyr Tyr Ala Glu Ser Val Lys
1               5                   10                  15

Gly

<210> SEQ ID NO 29
<211> LENGTH: 11
<212> TYPE: PRT
<213> ORGANISM: Artificial Sequence
<220> FEATURE:
<223> OTHER INFORMATION: Amino acid sequence of clone H754.6 variable
      region heavy chain CDR3

<400> SEQUENCE: 29

Asp Glu Val Ser Phe Tyr Tyr Gly Leu Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Amino acid sequence of clone H754.6 variable
      region light chain CDR1

<400> SEQUENCE: 30

Arg Ala Ser Gln Gly Ile Arg Asp Asp Leu Gly
1               5                   10

<210> SEQ ID NO 31
<211> LENGTH: 7
<212> TYPE: PRT
<213> ORGANISM: Artificial Sequence
<220> FEATURE:
```

<223> OTHER INFORMATION: Amino acid sequence of clone H754.6 variable
      region light chain CDR2

<400> SEQUENCE: 31

Ala Ala Ser Ser Leu Gln Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Amino acid sequence of clone H754.6 variable
      region light chain CDR3

<400> SEQUENCE: 32

Leu Gln His Asn Ser Tyr Pro Tyr Thr
1               5

<210> SEQ ID NO 33
<211> LENGTH: 238
<212> TYPE: PRT
<213> ORGANISM: Homo sapiens

<400> SEQUENCE: 33

Met Leu Thr Thr Leu Leu Pro Ile Leu Leu Leu Ser Gly Trp Ala Phe
1               5                   10                  15

Cys Ser Gln Asp Ala Ser Asp Gly Leu Gln Arg Leu His Met Leu Gln
                20                  25                  30

Ile Ser Tyr Phe Arg Asp Pro Tyr His Val Trp Tyr Gln Gly Asn Ala
            35                  40                  45

Ser Leu Gly Gly His Leu Thr His Val Leu Glu Gly Pro Asp Thr Asn
        50                  55                  60

Thr Thr Ile Ile Gln Leu Gln Pro Leu Gln Glu Pro Glu Ser Trp Ala
65                  70                  75                  80

Arg Thr Gln Ser Gly Leu Gln Ser Tyr Leu Leu Gln Phe His Gly Leu
                85                  90                  95

Val Arg Leu Val His Gln Glu Arg Thr Leu Ala Phe Pro Leu Thr Ile
                100                 105                 110

Arg Cys Phe Leu Gly Cys Glu Leu Pro Pro Glu Gly Ser Arg Ala His
            115                 120                 125

Val Phe Phe Glu Val Ala Val Asn Gly Ser Ser Phe Val Ser Phe Arg
        130                 135                 140

Pro Glu Arg Ala Leu Trp Gln Ala Asp Thr Gln Val Thr Ser Gly Val
145                 150                 155                 160

Val Thr Phe Thr Leu Gln Gln Leu Asn Ala Tyr Asn Arg Thr Arg Tyr
                165                 170                 175

Glu Leu Arg Glu Phe Leu Glu Asp Thr Cys Val Gln Tyr Val Gln Lys
                180                 185                 190

His Ile Ser Ala Glu Asn Thr Lys Gly Ser Gln Thr Ser Arg Ser Tyr
            195                 200                 205

Thr Ser Leu Val Leu Gly Val Leu Val Gly Gly Phe Ile Ile Ala Gly
        210                 215                 220

Val Ala Val Gly Ile Phe Leu Cys Thr Gly Gly Arg Arg Cys
225                 230                 235

ANTIBODIES AGAINST HEPCR

TECHNICAL FIELD OF THE INVENTION

The present invention relates to antibodies for use in the treatment of disease, particularly prostate cancer, and especially metastatic and aggressive prostate cancer. The present invention particularly relates to monoclonal antibodies against human endothelial protein C receptor (hEPCR).

BACKGROUND TO THE INVENTION

Prostate cancer is the most common cancer in men and the most common cause of cancer death in men in the UK. According to Cancer Research UK statistics, in 2016, over 47000 men were diagnosed with prostate cancer and 11631 deaths were recorded. Many of these deaths were at least partly attributable to the absence of efficient therapies that target aggressive prostate cancer, responsible for cancer chemo-resistance and recurrence. Cancer stem cells and related invasive cancer cells have been associated with cancer relapse and recurrence in patients that have been treated with chemotherapy and radiotherapy. Developing therapeutic strategies that target these populations has therefore a potential to significantly impact and improve the treatment and survival of patients with aggressive and therapy-resistant prostate disease.

Aggressive prostate cancer is responsible for the yearly death of over 11,000 men in the UK. Unfortunately, there are no successful therapies for the treatment of patients with this recurrent form of prostate cancer. A population of aggressive prostate cancer cells has been discovered, the presence of which within patients' cancerous tissues correlates with poor prognosis and decreased patients' survival. This population of cancer cells have been used to identify potential targets for antibody-based therapy. The human Endothelial Protein C Receptor (hEPCR also known as CD201) has been identified as a suitable target for this therapy due to the absence of its expression in normal prostate and its low/absence of overall expression in other tissues and organs of the human body. The expression of the hEPCR on the cell surface also makes this molecule a suitable target for antibody therapy. Although, hEPCR has been shown to be associated with aggressive cancers, and although hEPCR antibodies for research applications are commercially available, there are no antibody-based therapies that target hEPCR in aggressive cancers. Traditional cancer treatments such as chemotherapy, radiotherapy, immunotherapies and hormone therapies are unsuccessful against this form of recurrent cancer. Thus, developing a therapy that target this form of cancer is essential.

It would therefore be advantageous to generate monoclonal antibodies for targeting cancer stem cells and invasive and/or aggressive prostate cancer, aimed at contributing toward developing an antibody-based therapy against aggressive prostate cancer and other types of cancer. In this regard, hEPCR is also expressed by breast and ovarian cancers and therefore, the hEPCR antibodies are suitable to target both cancers.

It would also be advantageous to provide hEPCR antibodies capable of targeting and/or neutralising invasive and aggressive prostate cancer, and other cancers such as breast and ovarian.

SUMMARY OF THE INVENTION

According to a first aspect of the invention there is provided an antibody or antigen binding fragment thereof that binds to human EPCR (hEPCR), wherein the antibody comprises a light chain variable region and a heavy chain variable region, wherein the heavy chain variable region comprises:
(a) a heavy chain CDR1 comprising an amino acid sequence selected from SEQ ID NO: 9, 15, 21 and 27;
(b) a heavy chain CDR2 comprising an amino acid sequence selected from SEQ ID NO: 10, 16, 22 and 28; and
(c) a heavy chain CDR3 comprising an amino acid sequence selected from SEQ ID NO: 11, 17, 23, and 29
and wherein the light chain variable region comprises:
(a) a light chain CDR1 comprising an amino acid sequence selected from SEQ ID NO: 12, 18, 24 and 30;
(b) a light chain CDR2 comprising an amino acid sequence selected from SEQ ID NO: 13, 19, 25 and 31; and
(c) a light chain CDR3 comprising an amino acid sequence selected from SEQ ID NO: 14, 20, 26 and 32.

In some embodiments the antibody comprises a light chain variable region and a heavy chain variable region, wherein the heavy chain variable region comprises:
(a) a heavy chain CDR1 comprising the amino acid sequence of SEQ ID NO:9,
(b) a heavy chain CDR2 comprising the amino acid sequence of SEQ ID NO:10; and
(c) a heavy chain CDR3 comprising the amino acid sequence of SEQ ID NO:11
and wherein the light chain variable region comprises:
(a) a light chain CDR1 comprising the amino acid sequence of SEQ ID NO:12;
(b) a light chain CDR2 comprising the amino acid sequence of SEQ ID NO:13; and
(c) a light chain CDR3 comprising the amino acid sequence selected from SEQ ID NO:14.

In some embodiments the antibody comprises a light chain variable region and a heavy chain variable region, wherein the heavy chain variable region comprises:
(a) a heavy chain CDR1 comprising the amino acid sequence of SEQ ID NO:15,
(b) a heavy chain CDR2 comprising the amino acid sequence of SEQ ID NO:16; and
(c) a heavy chain CDR3 comprising the amino acid sequence of SEQ ID NO:17 and wherein the light chain variable region comprises:
(a) a light chain CDR1 comprising the amino acid sequence of SEQ ID NO:18;
(b) a light chain CDR2 comprising the amino acid sequence of SEQ ID NO:19; and
(c) a light chain CDR3 comprising the amino acid sequence of SEQ ID NO:20.

In some embodiments the antibody comprises a light chain variable region and a heavy chain variable region, wherein the heavy chain variable region comprises:
(a) a heavy chain CDR1 comprising the amino acid sequence of SEQ ID NO:21,
(b) a heavy chain CDR2 comprising the amino acid sequence of SEQ ID NO:22; and
(c) a heavy chain CDR3 comprising the amino acid sequence of SEQ ID NO:23
and wherein the light chain variable region comprises:
(a) a light chain CDR1 comprising the amino acid sequence of SEQ ID NO:24;
(b) a light chain CDR2 comprising the amino acid sequence of SEQ ID NO:25; and
(c) a light chain CDR3 comprising the amino acid sequence of SEQ ID NO:26.

In some embodiments the antibody comprises a light chain variable region and a heavy chain variable region, wherein the heavy chain variable region comprises:
(a) a heavy chain CDR1 comprising the amino acid sequence of SEQ ID NO:27,
(b) a heavy chain CDR2 comprising the amino acid sequence of SEQ ID NO:28; and
(c) a heavy chain CDR3 comprising the amino acid sequence of SEQ ID NO:29
and wherein the light chain variable region comprises:
(a) a light chain CDR1 comprising the amino acid sequence of SEQ ID NO:30;
(b) a light chain CDR2 comprising the amino acid sequence of SEQ ID NO:31; and
(c) a light chain CDR3 comprising the amino acid sequence of SEQ ID NO:32.

It has been surprisingly found that antibody and antibody fragments of the invention are effective at treating aggressive and/or metastatic prostate cancer. Since no effective hEPCR-binding antigens have been used to treat aggressive and/or metastatic prostate cancer to date, it is surprising that the antibodies and antibody fragments of the invention are able to treat such cancer, when other treatments have failed.

According to a second aspect of the invention there is provided an isolated antibody or antigen-binding fragment thereof that binds human endothelial protein C receptor (hEPCR) (the sequence of which is given in SEQ ID NO: 33 (found at: https://www.ncbi.nlm.nih.gov/protein/AAH14451.1)) and neutralizes, reduces or interferes with, at least one activity of hEPCR, wherein: (a) the antibody or antigen-binding fragment comprises a heavy chain variable region (HCVR) with at least 80% identity to a sequence selected from SEQ ID NO: 1, 3, 5 and 7, and/or a light chain variable region (LCVR) with at least 80% identity to a sequence selected from SEQ ID NO: 2, 4, 6 and 8; and/or (b) the antibody or antigen-binding fragment comprises a heavy chain variable region (HCVR) selected from SEQ ID NO: 1, 3, 5 and 7 with 10 or fewer conservative amino acid substitutions and/or a light chain variable region (LCVR) selected from SEQ ID NO: 2, 4, 6 and 8 with 10 or fewer conservative amino acid substitutions.

In some embodiments the antibody or antigen-binding fragment comprises a heavy chain variable region (HCVR) with at least 85, 90, 95, 96, 97, 98, 99 or 100% identity to a sequence selected from SEQ ID NO: 1, 3, 5 and 7, and/or a light chain variable region (LCVR) with at least 85, 90, 95, 96, 97, 98, 99 or 100% identity to a sequence selected from SEQ ID NO: 2, 4, 6 and 8.

In some embodiments the antibody or antigen binding fragment comprises a heavy chain variable region with according to SEQ ID NO: 1 or a variant of that sequence having 1, 2 or 3 amino acid substitutions and a light chain variable region according to SEQ ID NO: 2 or a variant of that sequence having 1, 2 or 3 amino acid substitutions.

In some embodiments the antibody or antigen binding fragment comprises a heavy chain variable region according to SEQ ID NO: 3 or a variant of that sequence having 1, 2 or 3 amino acid substitutions and a light chain variable region according to SEQ ID NO: 4 or a variant of that sequence having 1, 2 or 3 amino acid substitutions.

In some embodiments the antibody or antigen binding fragment comprises a heavy chain variable region according to SEQ ID NO: 5 or a variant of that sequence having 1, 2 or 3 amino acid substitutions and a light chain variable region according to SEQ ID NO: 6 or a variant of that sequence having 1, 2 or 3 amino acid substitutions.

In some embodiments the antibody or antigen binding fragment comprises a heavy chain variable region according to SEQ ID NO: 7 or a variant of that sequence having 1, 2 or 3 amino acid substitutions and a light chain variable region according to SEQ ID NO: 8 or a variant of that sequence having 1, 2 or 3 amino acid substitutions.

In some embodiments the antibody or antigen binding fragment comprises a heavy chain variable region with at least 85, 90, 95, 96, 97, 98, 99 or 100% identity to SEQ ID NO: 1 and a light chain variable region with at least 85, 90, 95, 96, 97, 98, 99 or 100% identity to SEQ ID NO: 2.

In some embodiments the antibody or antigen binding fragment comprises a heavy chain variable region with at least 85, 90, 95, 96, 97, 98, 99 or 100% identity to SEQ ID NO: 3 and a light chain variable region with at least 85, 90, 95, 96, 97, 98, 99 or 100% identity to SEQ ID NO: 4.

In some embodiments the antibody or antigen binding fragment comprises a heavy chain variable region with at least 85, 90, 95, 96, 97, 98, 99 or 100% identity to SEQ ID NO: 5 and a light chain variable region with at least 85, 90, 95, 96, 97, 98, 99 or 100% identity to SEQ ID NO: 6.

In some embodiments the antibody or antigen binding fragment comprises a heavy chain variable region with at least 85, 90, 95, 96, 97, 98, 99 or 100% identity to SEQ ID NO: 7 and a light chain variable region with at least 85, 90, 95, 96, 97, 98, 99 or 100% identity to SEQ ID NO: 8.

The present invention therefore provides isolated binding molecules that bind to human endothelial protein C receptor (hEPCR), and which are able to target and/or neutralise aggressive cancers, such as aggressive prostate cancer.

In some embodiments the antibody or antigen binding fragment thereof of the first or second aspects of the invention is a human antibody or is a bispecific, chimeric, humanized or deimmunized antibody.

In some embodiments, the antibody or antigen binding fragment thereof is a monoclonal antibody.

According to a third aspect of the invention there is provided a nucleic acid molecule encoding the antibody or antigen binding fragment of either the first or second aspects of the invention.

According to a fourth aspect of the invention there is provided a vector comprising at least one nucleic acid molecule of the third aspect of the invention.

According to a fifth aspect of the invention there is provided a host cell comprising a vector of the fourth aspect of the invention, preferably wherein the host cell is derived from a mammal or insect.

According to a sixth aspect of the invention there is provided an antibody or antigen binding fragment of the first or second aspects of the invention for use in the treatment of cancer, preferably prostate cancer. The prostate cancer may be aggressive and/or metastatic prostate cancer.

According to a seventh aspect of the invention there is provided a pharmaceutical composition comprising the antibody or antigen binding fragment of the first or second aspect of the invention and one or more pharmaceutically acceptable diluents or excipients. Particularly suitable diluents or excipients include phosphate buffered saline (PBS).

In some embodiments the composition is suitable for parenteral administration into the human body, for example by intravenous, intramuscular, intradermal, intraperitoneal, intratumor, intravesical, intra-arterial, intrathecal, intra-capsular, intra-orbital, intracardiac, transtracheal, intra-articular, subcapsular, subarachnoid, intraspinal, epidural, intrasternal or subcutaneous administration.

As used herein, the term "binding molecule" encompasses (1) an antibody, (2) an antigen-binding fragment of an antibody, and (3) a derivative of an antibody, each as defined hereinabove for the first or second aspects of the invention. The term "binds to hEPCR" or "binding to hEPCR" refers to the binding of a binding molecule, as defined herein, to the hEPCR in an in vitro assay, such as a BIAcore assay or by Octet (surface plasmon resonance). The binding molecule preferably has a binding affinity (Kd) of $1\times10^{-6}$M or less, more preferably less than $50\times10^{-7}$M, still more preferably less than $1\times10^{-7}$M.

As used herein, the term "isolated antibody" or "isolated binding molecule" refers to an antibody or a binding molecule that: (1) is not associated with naturally associated components that accompany it in its native state; (2) is free of other proteins from the same species; (3) is expressed by a cell from a different species; or (4) does not occur in nature. Examples of isolated antibodies include an anti-hEPCR antibody that has been affinity purified using hEPCR, an anti-hEPCR antibody that has been generated by hybridomas or other cell lines in vitro, and a human anti-hEPCR antibody derived from a transgenic animal.

The term "antibody" refers to an immunoglobulin molecule that is typically composed of two identical pairs of polypeptide chains, each pair having one "heavy" (H) chain and one "light" (L) chain. Human light chains are classified as kappa (κ) and lambda (λ). Heavy chains are classified as mu, delta, gamma, alpha, or epsilon, and define the antibody's isotype as IgM, IgD, IgG, IgA, and IgE, respectively. Each heavy chain comprises a heavy chain variable region (abbreviated herein as HCVR or VH) and a heavy chain constant region. The heavy chain constant regions of IgD, IgG, and IgA comprise three domains, CH1, CH2 and CH3, and the heavy chain constant regions of IgM and IgE comprise four domains, CH1, CH2, CH3, and CH4. Each light chain comprises a light chain variable region (abbreviated herein as LCVR or VL) and a light chain constant region. The light chain constant region comprises one domain, CL. The constant regions of the antibodies may mediate the binding of the immunoglobulin to host tissues or factors, including various cells of the immune system (e.g., effector cells). The VH and VL regions can be further subdivided into regions of hypervariability, termed complementarity determining regions (CDR), interspersed with regions that are more conserved, termed framework regions (FR). Each VH and VL comprises three CDRs and four FRs, arranged from the amino-terminus to carboxy-terminus in the following order: FR1, CDR1, FR2, CDR2, FR3, CDR3, FR4. The variable regions of each heavy/light chain pair (VH and VL), respectively, form the antibody binding site. The assignment of amino acids to each region or domain is in accordance with the definitions of Kabat Sequences of Proteins of Immunological Interest (National Institutes of Health, Bethesda, Md. (1987 and 1991)) or in accordance with the definitions of Chothia et al. Conformations of immunoglobulin hypervariable regions (Nature 1989; 342 (6252):877-83).

The term "antibody" encompasses an antibody that is a multimeric form of antibodies, such as dimers, trimers, or higher-order multimers of monomeric antibodies. It also encompasses an antibody that is linked or attached to a non-antibody moiety. Further, the term "antibody" is not limited by any particular method of producing the antibody. For example, it includes monoclonal antibodies, recombinant antibodies and polyclonal antibodies.

Another aspect of the invention provides a method of treating cancer in a mammal, comprising administering to the mammal a therapeutically effective amount of a binding molecule as described herein. The mammal may be a human.

In another aspect of the invention, there is provided a method of preventing cancer in a mammal, comprising administering to the mammal a therapeutically effective amount of a binding molecule as described herein.

The cancer may be selected from prostate, ovarian and breast cancer, but is preferably prostate cancer, and more preferably aggressive and/or metastatic prostate cancer.

The term "preventing cancer" or "prevention of cancer" refers to delaying, inhibiting, or preventing the onset of a cancer in a mammal in which the onset of oncogenesis or tumorigenesis is not evidenced but a predisposition for cancer is identified whether determined by genetic screening, for example, or otherwise. The term also encompasses treating a mammal having premalignant conditions to stop the progression of, or cause regression of, the premalignant conditions towards malignancy. Examples of premalignant conditions include hyperplasia, dysplasia, and metaplasia.

In some embodiments, the binding molecules may be administered alone as monotherapy, or administered in combination with one or more additional therapeutic agents or therapies. Thus, in another embodiment of the invention is provided a method of treating or preventing cancer by a combination therapy, which method comprises administering a binding molecule as disclosed herein, in combination with one or more additional therapies or therapeutic agents. The term "additional therapy" refers to a therapy which does not employ a binding molecule provided by the disclosure as a therapeutic agent. The term "additional therapeutic agent" refers to any therapeutic agent other than a binding molecule provided by the disclosure.

The binding molecules and compositions provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. The suitable route and method of administration may vary depending on a number of factors such as the specific antibody being used, the rate of absorption desired, specific formulation or dosage form used, type or severity of the disorder being treated, the specific site of action, and conditions of the patient, and can be readily selected by a person skilled in the art.

The term "therapeutically effective amount" of a binding molecule refers to an amount that is effective for an intended therapeutic purpose. For example, in the context of enhancing an immune response, a "therapeutically effective amount" is any amount that is effective in stimulating, evoking, increasing, improving, or augmenting any response of a mammal's immune system. In the context of treating cancer, a "therapeutically effective amount" is any amount that is sufficient to cause any desirable or beneficial effect in the mammal being treated, such as inhibition of further growth or spread of cancer cells, death of cancer cells, inhibition of reoccurrence of cancer, reduction of pain associated with the cancer, or improved survival of the mammal. In a method of preventing cancer, a "therapeutically effective amount" is any amount that is effective in delaying, inhibiting, or preventing the onset of a cancer in the mammal to which the binding molecule is administered.

The therapeutically effective amount of a binding molecule usually ranges from about 0.001 to about 500 mg/kg, and more usually about 0.05 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the therapeutically effective amount of an anti-human CD134 antibody is in the range of about 0.1-30 mg/kg of body weight of the mammal. The precise dosage level to be administered can be readily determined by a person skilled in the art and will depend on a number of factors, such as the type, and severity of the disorder to be treated, the particular binding molecule employed, the route of administration, the time of administration, the duration of the treatment, the particular additional therapy employed, the age, sex, weight, condition, general health and prior medical history of the patient being treated, and like factors well known in the art.

A binding molecule or composition is usually administered on multiple occasions. Intervals between single doses can be, for example, weekly, monthly, every three months or yearly. An exemplary treatment regimen entails administration once per week, once every two weeks, once every three weeks, once every four weeks, once a month, once every 3 months or once every three to 6 months. Typical dosage regimens for an anti-hEPCR antibody include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

Sequences

The amino acid sequences referred to in the present invention are as follows (in an N-terminal to C-terminal order; represented in the one-letter amino acid code):

```
                                                        SEQ ID NO: 1
(Region of the Heavy Chain Variable Domain of anti-hEPCR clone
H61.3):
QVQLQQWGAGLLKPSETLSLTCAVYGGSFSGYYWSWIRQPPGKGLEWIG

EINHSGSTNYNPSLKSRVTISVDTSKNQFSLKLSSVTAADTAVYYCARRQLIASSY

AFDIWGQGTMVTVSS

SEQ ID NO: 2
(Region of the Light Chain Variable Domain of anti-hEPCR clone
H61.3):
EIVMTQSPATLSLSPGERATLSCRASQSVTTRYLSWYQQKPGQAPRLLIYG

ASTRATGIPARFTGSGSGTDFTLTISSLQPEDFAVYYCQQDYNLFTFGPGTKVDIK

SEQ ID NO: 3
(Region of the Heavy Chain Variable Domain of anti-hEPCR clone
H589.9):
EVQLLESGGGLVQPGGSLRLSCAASGFTFSSYAMSWVRQAPGKGLEWVS

GSSGSGGSAFYADFVKGRFTISRDISKNTLFLQMNSLRAEDTAVYYCAKEGTISM

AFDIWGQGTTVTVSS

SEQ ID NO: 4
(Region of the Light Chain Variable Domain of anti-hEPCR clone
H589.9):
AIQMTQSPSSLSASVGDRVTITCRASQGIRNDLGWYQQKPGKAPKLLICA

ASSLQSGVPSRFSGRGSGTDFTLTISSLQPEDFATYYCLQDYNYPRTFGQGTKVEI

K

SEQ ID NO: 5
(Region of the Heavy Chain Variable Domain of anti-hEPCR clone
H599.5):
QVQLQESGPGLVQPSETLSLTCTVSGGSISSYYWSWIRQPPGKGLEWIGYI

YYSGSTNYNPSLKSRVTISVDTSKNQFSLKLSSVTAADTAVYYCARDQVNGWYR

TGFDYWGQGTLVTVSS

SEQ ID NO: 6
(Region of the Light Chain Variable Domain of anti-hEPCR clone
H599.5):
EIVMTQSPATLSLSPGERATLSCRASQSVSSGYLSWYQQKPGQAPRLLIYG

ASTRATGIPARFSGSGSGTDFTLTISSLQPEDFAAYYCQQDYNLPYTFGRGSKLEI

K

SEQ ID NO: 7
(Region of the Heavy Chain Variable Domain of anti-hEPCR clone
H754.6):
QVQLVESGGGLVTPGGSLRLSCAASGFTFSDYYMTWIRQAPGKGLEWVS

YISNSGYTIYYAESVKGRFTISRDNAKSSLYLQMNSLRAEDTAVYYCARDEVSFY

YGLDVWGQGTTVTVSS
```

```
                                                     SEQ ID NO: 8
(Region of the Light Chain Variable Domain of anti-hEPCR clone
H754.6):
DIQMTQSPSSLSASAGDRVTITCRASQGIRDDLGWYQQKPGQAPKRLIYA

ASSLQSGVPSRFSGSGSGTEFTLTISSLQPEDFATYYCLQHNSYPYTFGQGTKLEIK

SEQ ID NO: 9
(CDR1 region of the Heavy Chain Variable Domain of anti-
hEPCR clone H61.3):
GYYWS SEQ ID NO: 10
(CDR2 region of the Heavy Chain Variable Domain of anti-
hEPCR clone H61.3):
EINHSGSTNYNPSLKS SEQ ID NO: 11
(CDR3 region of the Heavy Chain Variable Domain of anti-
hEPCR clone H61.3):
RQLIASSYAFDI SEQ ID NO: 12
(CDR1 region of the Light Chain Variable Domain of anti-
hEPCR clone H61.3):
RASQSVTTRYLS SEQ ID NO: 13
(CDR2 region of the Light Chain Variable Domain of anti-
hEPCR clone H61.3):
GASTRAT SEQ ID NO: 14
(CDR3 region of the Light Chain Variable Domain of anti-
hEPCR clone H61.3):
QQDYNLFT SEQ ID NO: 15
(CDR1 region of the Heavy Chain Variable Domain of anti-
hEPCR clone H589.9):
SYAMS SEQ ID NO: 16
(CDR2 region of the Heavy Chain Variable Domain of anti-
hEPCR clone H589.9):
GSSGSGGSAFYADFVKG SEQ ID NO: 17
(CDR3 region of the Heavy Chain Variable Domain of anti-
hEPCR clone H589.9):
EGTISMAFDI SEQ ID NO: 18
(CDR1 region of the Light Chain Variable Domain of anti-
hEPCR clone H589.9):
RASQGIRNDLG SEQ ID NO: 19
(CDR2 region of the Light Chain Variable Domain of anti-
hEPCR clone H589.9):
AASSLQS SEQ ID NO: 20
(CDR3 region of the Light Chain Variable Domain of anti-
hEPCR clone H589.9):
LQDYNYPRT SEQ ID NO: 21
(CDR1 region of the Heavy Chain Variable Domain of anti-
hEPCR clone H599.5):
SYYWS SEQ ID NO: 22
(CDR2 region of the Heavy Chain Variable Domain of anti-
hEPCR clone H599.5):
YIYYSGSTNYNPSLKS
```

-continued

SEQ ID NO: 23
(CDR3 region of the Heavy Chain Variable Domain of anti-
hEPCR clone H599.5):
DQVNGWYRTGFDY SEQ ID NO: 24
(CDR1 region of the Light Chain Variable Domain of anti-
hEPCR clone H599.5):
RASQSVSSGYLS SEQ ID NO: 25
(CDR2 region of the Light Chain Variable Domain of anti-
hEPCR clone H599.5):
GASTRAT SEQ ID NO: 26
(CDR3 region of the Light Chain Variable Domain of anti-
hEPCR clone H599.5):
QQDYNLPYT SEQ ID NO: 27
(CDR1 region of the Heavy Chain Variable Domain of anti-
hEPCR clone H754.6):
DYYMT SEQ ID NO: 28
(CDR2 region of the Heavy Chain Variable Domain of anti-
hEPCR clone H754.6):
YISNSGYTIYYAESVKG SEQ ID NO: 29
(CDR3 region of the Heavy Chain Variable Domain of anti-
hEPCR clone H754.6):
DEVSFYYGLDV SEQ ID NO: 30
(CDR1 region of the Light Chain Variable Domain of anti-
hEPCR clone H754.6):
RASQGIRDDLG SEQ ID NO: 31
(CDR2 region of the Light Chain Variable Domain of anti-
hEPCR clone H754.6):
AASSLQS SEQ ID NO: 32
(CDR3 region of the Light Chain Variable Domain of anti-
hEPCR clone H754.6):
LQHNSYPYT SEQ ID NO: 33
(amino acid sequence of hEPCR)
MLTTLLPILLLSGWAFCSQDASDGLQRLHMLQISYFRDPYHVWYQGNAS

LGGHLTHVLEGPDTNTTIIQLQPLQEPESWARTQSGLQSYLLQFHGLVRLVHQER

TLAFPLTIRCFLGCELPPEGSRAHVFFEVAVNGSSFVSFRPERALWQADTQVTSG

VVTFTLQQLNAYNRTRYELREFLEDTCVQYVQKHISAENTKGSQTSRSYTSLVL

GVLVGGFIIAGVAVGIFLCTGGRRC

DETAILED DESCRIPTION OF THE INVENTION

In order that the invention may be more clearly understood embodiments thereof will now be described, by way of example only, with reference to the accompanying drawings, of which:

FIG. 7 is a table providing the measurements of the cytotoxic effects of the antibody clones against cell line PC3

EXAMPLES

1. Mouse Immunisation

Mouse: 129-CA19=HHKKL-L-DOB: Aug. 8, 2016

Figure 1:
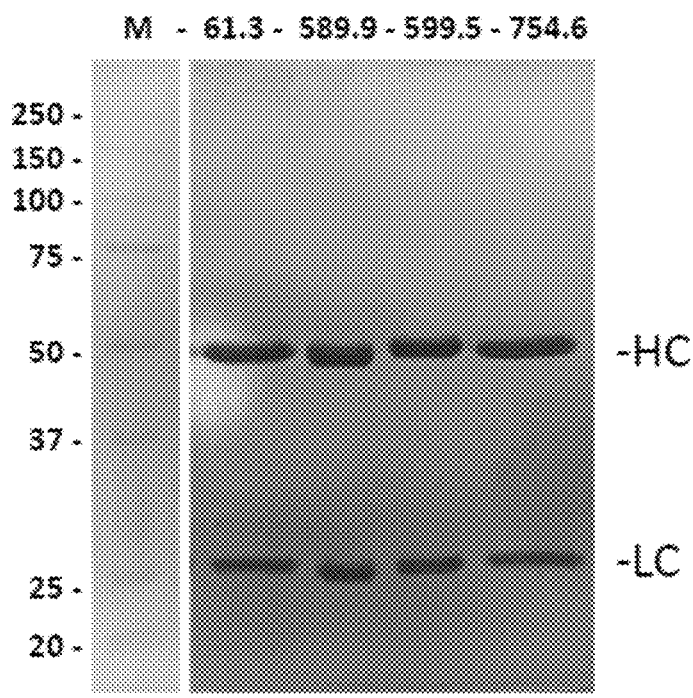
FIG. 1 is an image of an SDS Page gel illustrating the heavy chain and light chain molecular weights of antibodies derived from hybridoma clones H61.3, H589.9, H599.5 and H754.6.

Immunisation with recombinant human EPCR (human PROCR-His Tag, Sino Biological, ref. 13320-H08H) was performed as follows:

1st shot: with 30 μg protein on day 1+alum

1st boost: with 20 μg protein after one month+alum

2nd boost: with 20 μg protein after approximately 2.5 months+alum

3rd boost: with 20 μg protein after approximately 3.5 months+alum final boost: with 20 μg protein on after approximately 4.5 months without alum 2. Generation of Hybridomas: Fusion of B-Cells with the Fusion Cell-Partner: SP2/0

Media used: R10 (RPMI+10% FCS (Fetal Calf Serum)

R0+(RPMI+2% L-glutamine+1% Pen/Strep+1% Na Pyruvate+0.1% 2-mercaptoethanol)

R10+(RPMI+10% FCS+2% L-glutamine+OPI supplement (5 mL—Sigma)+HAT supplement (1 vial—Sigma) 1% Pen/Strep+1% Na Pyruvate+0.1% 2-mercaptoethanol)

ECF buffer (0.3 M Mannitol, 0.1 mM CaCl2, 0.1 mM MgCl2)

Instrument for electro cell fusion: ECFG21 No. 20130718—Nepagene

SP2/0 cells were grown in RPMI+10% FCS.

The ratio of spleen cells:SP2/0 was between 1:1 and 1:4.

Protocol:

The spleen was removed from the immunised mouse, 3-6 days after the final boost and the cells isolated.

The cells were counted: $9.5 \times 10^7$ B cells+$9.5 \times 10^7$ SP2/0.

The SP2/0 cells were collected, washed once in warm R0+ medium and pelletised.

Both pellets were combined and washed 2× with 20 mL warm ECF buffer then resuspended in 6.4 mL ECF buffer. The final density of cells was approximatively $2.0 \times 10^8$ in 6.4 mL.

The cell suspension was transferred into the electrofusion chamber, and ECF performed.

The cells were pipetted from the chamber and transferred to a tube with 20 mL warm R0+ and incubated for 10 mins at room temperature.

The cells were then centrifuged at 1200 rpm, 8 min, room temperature and resuspended in 500 mL R10+, before being plated in 96-wells plates as follows:

40 plates with $1.8 \times 10^4$ cells in 200 μL per well 50 plates with $8 \times 10^3$ cells in 200 μL per well Finally, the cells were incubated at 37° C. at 5% CO2.

3. Hybridomas Screening

Plates were screened by eye for growing hybridomas colonies, after approximately 7-14 days of incubation (the time required for the colonies to become visible).

150 μL of supernatant was collected from each well containing one single colony for further screenings (ELISA and flow cytometry)

The hybridomas found positive for specific anti-hEPCR IgG production were transferred to larger plates to be bulked up.

Hybridomas were then subcloned to ensure their stability.

4. Antibodies Production and Purification.

Four clones showed a signal when tested through flow cytometry and were stable, namely: H61.3, H589.9, H599.5 and H745.6. These four clones were then purified as follows:

Buffers: Buffers were prepared for purification in nanopure ddH2O. NaOH or HCl were used to adjust pH. The various buffers prepared are detailed below:

BINDING BUFFER: 20 mM sodium phosphate, pH 7.0

0.8175 g (12 mM) Na2HPO4-7H2O 0.28 g (8 mM) NaH2PO4-H2O

The pH was adjusted to 7.0 and the volume made up to 250 m L with ddH2O.

ELUTION BUFFER: 0.1 M GLYCINE-HCl, pH 2.7

0.375 g glycine

140 μL HCl

The pH was adjusted to 2.7 and the volume made up to 100 mL with ddH2O.

NEUTRALIZING BUFFER: 1 M Tris-HCl, pH 9.0

2.82 g Trisma-base

The pH was adjusted to 9.0 and the volume made up to 20 mL with ddH2O.

Purification kit: Protein G GraviTrap—GE Healthcare, ref: 12526518

Protocol:

Hybridomas were grown in at least 400 mL R10+ medium until they were 80-90% confluent then the medium was changed to CD-Hybridoma medium (Gibco, ref: 11279023)

The hybridomas were maintained in culture until approximately ⅓ were dead, then the cells pelleted and supernatant collected for purification.

The column storage solution was removed and the column placed in a Workmate® column stand.

The column was equilibrated with 10 ml of binding buffer and a sample added.

15 ml of binding buffer was then added to the columns.

The antibodies were eluted by adding 6 ml of elution buffer to the columns, followed by adding 1.2 mL of neutralising buffer to the tubes used for collecting the antibody-containing fractions.

After elution, the columns were regenerated by washing them with 5 to 10 ml of binding buffer.

5. Dialysis for Buffer Exchange Against PBS

After elution, the antibodies were dialysed against PBS, after which they are ready to use. The dialysis was performed as follows:

Dialysis cassette: Slide-A-Lyzer® dialysis cassettes—ThermoFisher Scientific, product ref: 66810.

Protocol:

The samples were loaded into the cassettes, according to the manufacturer's instructions.

The cassette was dialysed in PBS for 2 hours, preferably in a cold room (<20 C), with the PBS being changed 3 times and performing the last dialysis step overnight in cold room.

6. Analysis of Purity a. Protein assay

Reagents: DC™ Protein Assay—Bio Rad, ref: 5000112

A BSA standard curve was prepared for calibration (BSA standard stock: 1.35 mg/mL):

| Concentration | BSA standard volume | Buffer volume |
| --- | --- | --- |
| 1.35 mg | 20 μL | 0 μL |
| 1.00 mg | 14.8 μL | 5.2 μL |
| 0.8 mg | 11.85 μL | 8.14 μL |

| Concentration | BSA standard volume | Buffer volume |
| --- | --- | --- |
| 0.6 mg | 8.88 μL | 11.11 μL |
| 0.5 mg | 7.40 μL | 12.59 μL |
| 0.4 mg | 5.92 μL | 14.07 μL |
| 0.2 mg | 2.96 μL | 17.03 μL |
| 0 mg | 0 μL | 20 μL |

Using a flat bottom 96 wells plate, 5 μL of the standards and samples in triplicate were plated.

25 μL of solution A was added to each well. (Sol. A: 1 mL of reagent A+25 μL of reagent S)

200 μL of reagent B was added to each well (photosensitive, take an aliquot and keep in dark).

The plates were incubated at RT in dark for 10-15 minutes and read at 750 nm within an hour which yielded the following results:

H61.3—0.388 mg/mL in 6 mL=tot. 2.33 mg
H589.9—0.947 mg/mL in 3 mL=tot. 2.84 mg
H599.5—0.577 mg/mL in 7 mL=tot. 4.04 mg
H745.6—0.308 mg/mL in 6 mL=tot. 2.28 mg b. SDS-PAGE Coomassie Staining Solutions: GEL FIXING SOLUTION: 46% (v/v) MeOH, 7% (v/v) acetic acid in ddH2O COOMASSIE STAINING SOLUTION: 46% (v/v) MeOH, 7% (v/v) acetic acid, 0.1% (w/v) Coomassie Blue R-250 in ddH2O GEL DE-STAINING SOLUTION: 5% (v/v) MeOH, 7.5% (v/v) acetic acid in ddH2O Protocol:

The gel was fixed in 50 mL Gel Fixing solution for 1 hour

The gel was then stained with 50 mL Coomassie Staining solution for 1 hour.

Finally, the gel was destained in 50 mL De-staining solution for 24 hours.

The results are shown in FIG. 1.

7. Antibodies Validation a. ELISA

Buffers and Reagents:

Coating buffer: 15 mM Na2CO3+35 mM NaHCO3 in nanopure ddH2O—pH 9.6

Washing buffer: PBS+0.05% Tween-20

Blocking buffer: PBS+2% FCS

Stop Solution: 2N HsSO4 in ddH2O

TMB Substrate Set—Biolegend, ref: 421101

Test antibodies: H61.3, H589.9, H599.5, and H745.6

Primary mouse monoclonal antibodies anti-hEPCR (Sigma, ref: WH0010544M3-100 UG) and anti-MTSS1 (Sigma, ref: WH09788M1-50 UG) were used respectively as positive and negative controls.

All the antibodies were used at a concentration of 1 μg/mL in blocking buffer.

Protocol:

Coat one 96-well plate (mid-absorption) with 50 μL/well of hEPCR protein in coating buffer (0.5 μg/mL) at 4° C. overnight.

On the day of the assay, wash the plate 3× with washing buffer.

Block 30 min at room temperature (optional: ON at 4° C.) with 150-200 μL/well of blocking buffer.

Discard supernatant without washing.

Add 50 μL/well (optional 100 μL/well) of the test antibodies and incubate 1 h at room temperature.

Wash 3× with washing buffer.

Add 50 μL/well of secondary anti-mouse IgG-HRP in blocking buffer (1:3000) and incubate 1 h at room temperature.

Wash 3× with washing buffer.

Add 100 μL/well substrate.

Block reaction adding 50 μL/well Stop solution and measure at 450 nm.

Figure 2:
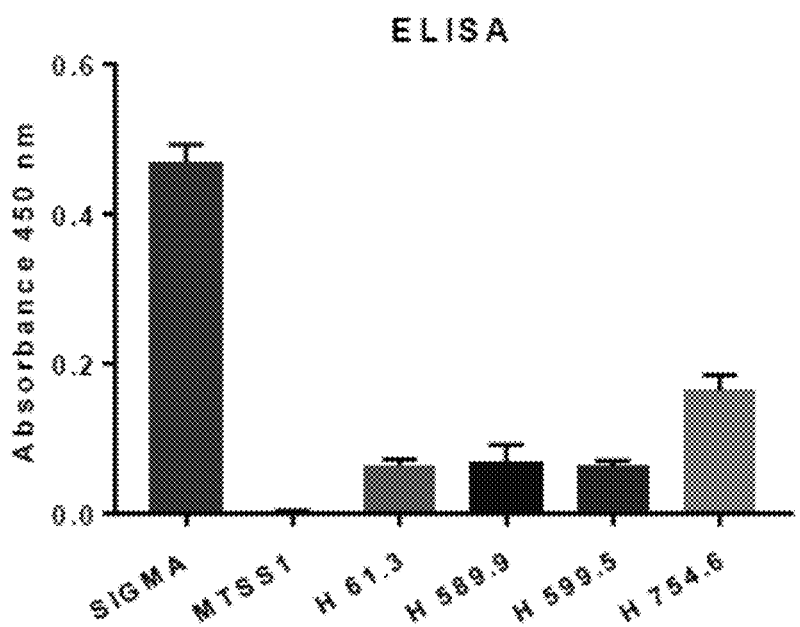
FIG. 2 is a bar graph illustrating the ELISA absorbance at 450 nm of antibodies from clones H61.3, H589.9, H599.5 and H754.6 against positive and negative controls.

The results are shown in the bar chart of FIG. 2 b. Flow Cytometry

Reagents: Donkey anti-Rat IgG (H+L) Highly Cross-Adsorbed, Alexa Fluor® 488

Goat anti-Mouse IgG (H+L) Highly Cross-Adsorbed, Alexa Fluor® 488

Tested antibodies: H61.3 H589.9 H599.5 H745.6

Primary rat monoclonal antibody anti-hEPCR (Sigma, ref: WH0010544M3-100 UG) was used as positive control.

Protocol:

Count DU145 cells: use 1.0×105 cells/tube.

Wash cells with 2 mL PBS, centrifuge 1200 rpm, 5'.

Discard supernatant and flick tubes to resuspend cells.

Add 45 μL PBS+5 μL Fc blocking reagent to each tube—gently vortex.

Incubate 15' at 4° C.

Add primary antibodies at 10 μg/mL, 50 μL/tube

Gently vortex tubes and incubate 30' at 4° C.

Wash cells twice with 2 mL PBS centrifuge 1200 rpm, 5'.

Discard supernatant and flick tubes to resuspend cells.

Add 100 μL/° secondary antibodies (1:500).

Incubate cells 30' at 4° C. in dark.

Wash cells with 2 mL PBS centrifuge 1200 rpm, 5'.

Discard supernatant and flick tubes to resuspend cells.

Add 300 μL ISOTON to each tube.

Acquire data with Beckman Coulter Gallios 11843225: Alexa 488 is detected on channel 1.

c. Western Blot

Reagents and buffer: 10× RUNNING BUFFER: 30.3 g Trizma base+144 g glycine+10 g SDS in 1 L dH2O 10× TRANSFER BUFFER: 30.3 g Trizma base+144 g glycine in 1 L dH2O 10% RESOLVING GEL: 4 mL dH2O+3.3 mL 30% acrylamide mix+2.5 mL 1.5M Tris pH 8.8+100 μL 10% SDS+100 μL 10% apS+4 μL TEMED 5% STACKING GEL: 4.1 mL dH2O+1 mL 30% acrylamide mix+750 μL 1M Tris pH 6.8+60 μL 10% SDS+60 μL 10% apS+6 μL TEMED Precision Plus Protein™ WesternC™ Standards—Biorad, ref. 161-0376

PVDF membrane: Amersham Hybond P0.45—GE Healthcare, ref. 10600023

2Ab Mouse HRP-linked—Cell signalling, ref. 70765

ECL Clarity Western—Biorad, 170-5061

Tested antibodies: H61.3 H589.9 H599.5 H745.6

Primary mouse monoclonal antibody anti-hEPCR (Sigma, ref: WH0010544M3-100 UG) was used as positive control.

Perform protein assay, load 30 μg of protein lysate from DU145 cells in each gel well.

In small eppendorfs add the required volume for each sample and then add ¼ of its volume of Laemmli buffer 5×+dye.

Boil samples at 99° C. for 10' before loading them into gels.

Load 5 μL of ladder to the far-left lane and then add all of the samples to each well in the same order.

Run the separating gel at 60 V for 10' and then at 100 V for the stacking gel in 1× running buffer.

Transfer proteins on PVDF membrane in 1× transfer buffer, 70V for 90'.

Block the membrane with 5% milk in TBST 1 hour at room temperature.

Probe membranes with 1 μg/mL primary antibodies in 5% milk/TBS at 4° C. overnight.

Wash 6×5' with TBST.

Probe membranes with secondary anti mouse-IgG antibody (1:1000) 1 hour at room temperature.

Wash 6×5' with TBST.

Develop membranes.

Figure 3:
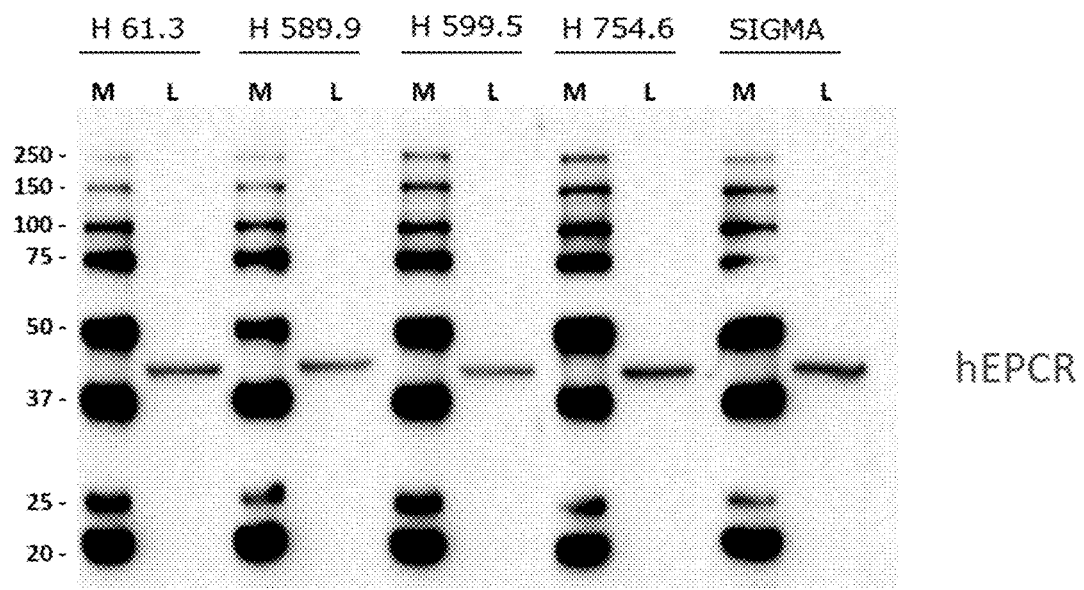
FIG. 3 is a Western Blot antibody validation analysis of antibodies H61.3, H589.9, H599.5 and H754.6 from clones against a positive control.

The results are shown in FIG. 3 e. ADCC (Antibody-Dependent Cellular Cytotoxicity) In Vitro Reporter Assay (In Vitro Killing Assay)

Reagents: mFcγRIV ADCC Reporter Bioassay, Core Kit—Promega, ref: M1211

Tested antibodies: H61.3, H589.9, H599.5, H745.6

Protocol: The ADCC Reporter Bioassay product protocol sheet was followed (available from Promega UK and Promega Corporation).

The cancer cells used were metastatic prostate cancer cells DU145 and PC3.

Figure 4:
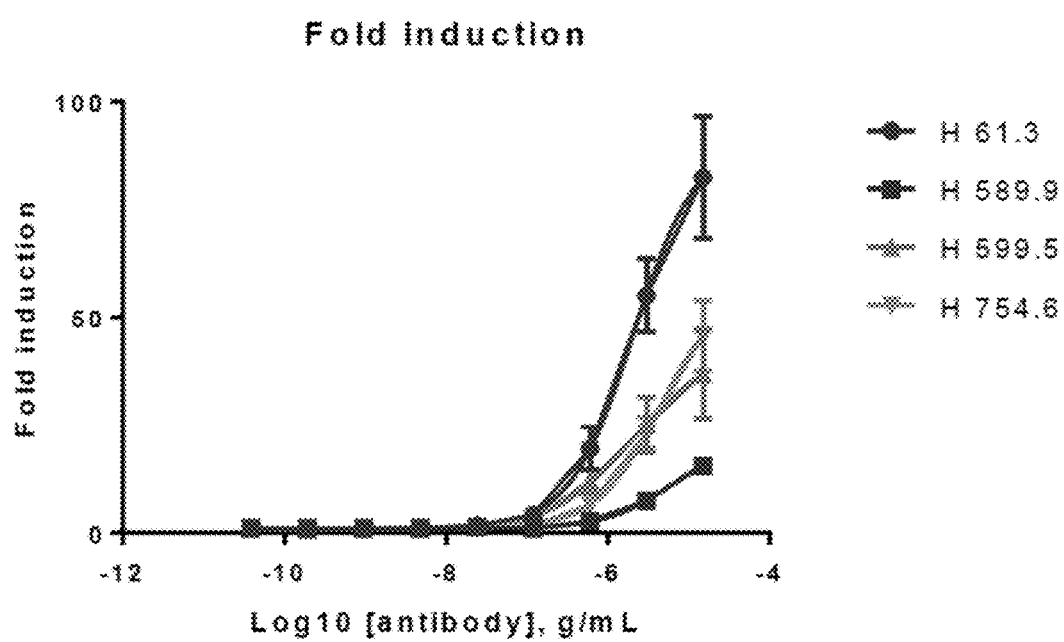
FIG. 4 is a graph illustrating the results of an in vitro killing assay, using antibodies from clones H61.3, H589.9, H599.5 and H754.6 binding to metastatic prostate cancer cells from the cell line DU145.
Figures 5, 6:
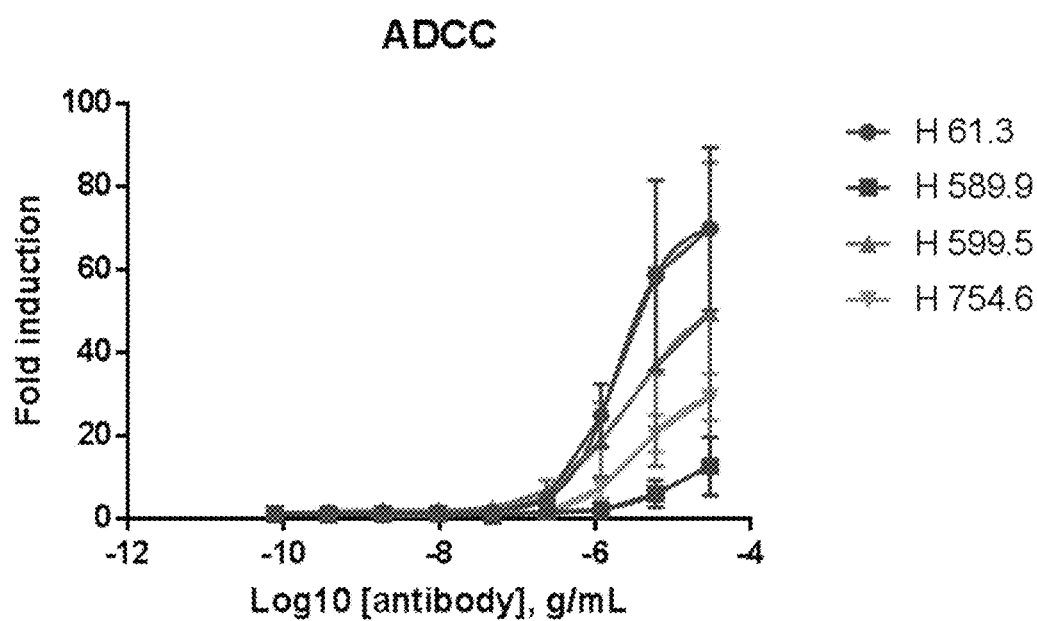
FIG. 5 is a table providing the measurements of the cytotoxic effects of the antibody clones against cell line DU145.
FIG. 6 is a graph illustrating the results of an in vitro killing assay, using antibodies from clones H61.3, H589.9, H599.5 and H754.6 binding to metastatic prostate cancer cells from the cell line PC3.

The results of the assay are shown FIGS. 4 and 5 (for DU145 cells) and FIGS. 6 and 7 (for PC3 cells). FIGS. 5 and 7 show underlying measurements depicted in the graphical results of FIGS. 4 and 6 respectively. The results in FIGS. 4 and 5 represent cytotoxic effects (killings) of each antibody against the DU145 prostate cancer cells, while the results of FIGS. 6 and 7 show the cytotoxic effects of each antibody against PC3 prostate cancer cells. Both PC3 and DU145 cell lines are aggressive and metastasize readily.

The results show the capacity of each antibody to induce cancer cells killing (cytotoxic effect). This is assessed by the Antibody-Dependent Cellular Cytotoxicity (ADCC) assay, which is a mechanism of cell-mediated immune defence that involves NK (Natural Killers) cells (effector cells) that interact with antibodies IgGs. This in vitro assay is essential for determining the therapeutic potential of an antibody. The results show that each antibody performed well at inducing cancer cell death. The highest cytotoxic capacity was obtained by the antibody H 61.3 against both cell lines. The inventors have surprisingly found that all four antibody clones are effective at killing multiple aggressive cancer cell lines, overcoming the current lack of hEPCR-binding agents able to halt or treat aggressive prostate cancers, and paving the way for a new immunotherapy treatment.

8. Antibody Sequencing from Clones 1161.3, 11589.9, 11599.5 and 11754.6

Sequencing was performed by whole transcriptome shotgun sequencing (RNA-Seq).

Hybridomas were cultured in IMDM medium containing 10% FBS and incubated at 37° C. in a 5% CO2 environment. Total RNA is extracted from cells and a barcoded cDNA library generated through RT-PCR using a random hexamer. Next Generation Sequencing was performed on an Illumina HiSeq sequencer. Contigs were assembled and data mined for antibody sequences identifying all viable antibody sequences (i.e. those not containing stop codons). Variable heavy and variable light domains were identified separately and relative abundance of each identified gene was reported in transcripts per million (TPM). The species and isotype of the identified antibody genes were confirmed. Sequences were compared with known aberrant (i.e. non-functional) antibody genes that are present in many hybridomas and these genes were removed from analysis when necessary.

The above embodiment is/embodiments are described by way of example only. Many variations are possible without departing from the scope of the invention as defined in the appended claims.

The invention claimed is:

1. An antibody or antigen binding fragment thereof that binds to human EPCR (hEPCR), wherein the antibody comprises a light chain variable region and a heavy chain variable region, wherein the heavy chain variable region comprises:
   (a) a heavy chain CDR1 comprising the amino acid sequence of SEQ ID NO: 9;
   (b) a heavy chain CDR2 comprising the amino acid sequence of SEQ ID NO: 10; and
   (c) a heavy chain CDR3 comprising the amino acid sequence of SEQ ID NO: 11;
   and wherein the light chain variable region comprises:
   (a) a light chain CDR1 comprising the amino acid sequence of SEQ ID NO: 12;
   (b) a light chain CDR2 comprising the amino acid sequence of SEQ ID NO: 13; and
   (c) a light chain CDR3 comprising the amino acid sequence of SEQ ID NO: 14.

2. The antibody or antigen-binding fragment thereof as claimed in claim 1, wherein the heavy chain and light chain regions comprise
   a heavy chain variable region with at least 85, 90, 95, 96, 97, 98, 99 or 100% identity to SEQ ID NO: 1 and a light chain variable region with at least 85, 90, 95, 96, 97, 98, 99 or 100% identity to SEQ ID NO: 2.

3. The antibody or antigen-binding fragment thereof as claimed in claim 1 wherein the antibody or fragment is a chimeric, humanized or deimmunized antibody or fragment thereof.

4. The antibody or antigen-binding fragment thereof as claimed in claim 1, wherein the antibody or antigen binding fragment is a monoclonal antibody or fragment thereof.

5. A nucleic acid molecule encoding the antibody or antigen binding fragment of claim 1.

6. A vector comprising at least one nucleic acid molecule of claim 5.

7. A host cell comprising a vector of claim 6, wherein the host cell is derived from a mammal or insect.

8. A method of treating cancer, comprising administering the antibody or antigen binding fragment of claim 1 to a subject in need thereof.

9. A pharmaceutical composition comprising the antibody or antigen binding fragment of claim 1 and one or more pharmaceutically acceptable diluents or excipients.

10. The pharmaceutical composition as claimed in claim 9, further comprising one or more additional therapeutic agents.

11. A method of treating cancer in a mammal, comprising administering to the mammal a therapeutically effective amount of the antibody or antigen binding fragment as claimed in claim 1.

12. The method 11, comprising administering a pharmaceutical composition as claimed in claim to a subject in need thereof.

* * * * *